United States Patent
Jani et al.

(10) Patent No.: US 8,257,835 B2
(45) Date of Patent: Sep. 4, 2012

(54) CERAMIC METAL COMPOSITE FOR ORTHOPAEDIC IMPLANTS

(75) Inventors: Shilesh C. Jani, Germantown, TN (US); Vivek Devidas Pawar, Germantown, TN (US); Carolyn L. Weaver, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 924 days.

(21) Appl. No.: 12/296,315

(22) PCT Filed: Apr. 11, 2007

(86) PCT No.: PCT/US2007/066434
§ 371 (c)(1), (2), (4) Date: Oct. 7, 2008

(87) PCT Pub. No.: WO2007/121242
PCT Pub. Date: Oct. 25, 2007

(65) Prior Publication Data
US 2009/0187255 A1    Jul. 23, 2009

Related U.S. Application Data

(60) Provisional application No. 60/790,918, filed on Apr. 11, 2006.

(51) Int. Cl.
*B32B 5/16* (2006.01)
*B32B 15/04* (2006.01)

(52) U.S. Cl. ........ 428/689; 428/325; 428/469; 428/688; 428/699

(58) Field of Classification Search ............ 428/469, 428/325, 688, 689, 699
See application file for complete search history.

(56) References Cited

U.S. PATENT DOCUMENTS
6,793,681 B1 * 9/2004 Pope et al. ............... 623/22.15

OTHER PUBLICATIONS

Dynamic Ceramic (http://www.dynacer.com/ZTA.htm) published online Sep. 2003.*
Correspondence from State Intellectual Property Office, P.R. China, including English translation of the first Office Action issued on Dec. 13, 2011.

* cited by examiner

*Primary Examiner* — Jennifer McNeil
*Assistant Examiner* — Lauren Robinson
(74) *Attorney, Agent, or Firm* — David A. Chambers, Esq.

(57) ABSTRACT

The invention relates to an orthopedic implant made of a ceramic metal composite. The composite (28, 48, 54) includes one phase that is a biocompatible metal or metal alloy and a second phase of ceramic particles examples of which include carbides, nitrides and/or oxides. In some embodiments, the implant comprises a homogeneous ceramic layer (24) as part of a multi-layered composition. In some embodiments, the multilayered composition comprises a homogeneous metal layer (32).

20 Claims, 2 Drawing Sheets

CERAMIC METAL COMPOSITE FOR ORTHOPAEDIC IMPLANTS

CROSS-REFERENCE TO RELATED APPLICATIONS

This application is a U.S. National Phase of PCT/US2007/066434 filed on Apr. 11, 2007, and claims priority to U.S. provisional patent application Ser. No. 60/790,918 filed Apr. 11, 2006, which is 2006. Each prior application is incorporated by reference as though fully described herein.

TECHNICAL FIELD

The present invention relates to ceramic/metal composite materials for orthopedic implants generally, and more specifically, to such materials for hip implants.

BACKGROUND OF THE INVENTION

For hip implants, the current standards of "hard-on-hard" bearings are ceramic-on-ceramic and metal-on-metal. The ceramics are inherently brittle in nature and are always associated with a finite risk of fracture. There are also limitations on the size of the ceramic components that can be made. Large size ceramic components (especially liners) have to be thin and may have higher risk of fracture. The metal-on-metal components have only insignificant fracture risk and larger size components can be made. The current standard material of metal-on-metal implants is high carbon Co—Cr (cobalt-chromium) alloy. The major concern with the metal-on-metal implant is the metal ion release from the joint and its unknown effects on the physiology of the human body. The advantage of metal-on-metal implants is that they can be used in larger sizes. The larger size of the implant allows greater range of motion. The metal-on-metal implants have also been shown to be useful for resurfacing types of applications where conservation of bone is desired. In such larger joints, conventional polyethylene or cross-linked polyethylene are not preferred as a counter-bearing surface and metal-on-metal is typically the only other alternative. This is due to the fact that the larger size requires a polyethylene liner to be thinner. A thinner liner may have less mechanical strength, may have increased creep, and may lead to increased wear and osteolysis and eventually to the failure of the implant.

The other commonly used hard-on-hard implant material is ceramic-on-ceramic. The current standard material of ceramic-on-ceramic implants is alumina. Metal ion release is typically not a concern for these implants. But due to limited toughness and the brittle nature of ceramics, it is difficult to make these implants in larger sizes. The ceramic components have finite probability of fracture thus leading to a potential joint failure and complications associated with the fracture of a joint.

It has been an object of much of the prior art to reduce the metal ion release and minimize the fracture risk by combining metal and ceramic components. One of the prior art approaches to reduce the risk of metal ion release is to use surface hardening of the head or liner or both using diffusion or plasma processes to incorporate nitrogen and/or carbon on the surface of the alloy. Another approach is to coat the metallic surface with ceramic coatings of nitrides (titanium nitride, chromium nitride, etc.), oxides (aluminum oxide, zirconium oxide, zirconium-alumina oxide, etc.) or diamond like carbon or diamond coatings. Another approach is to use a metal head on a ceramic liner or vice versa. In this approach, fracture risk is reduced along with the metal ion release.

Another approach that has been used is the reduction of the diametrical clearance between the articulating components thereby forming a thick lubricating film which assists in the reduction of wear. Fisher et al (U.S. Patent Publication No. 2005/0033442) and Khandkar et al. (U.S. Pat. No. 6,881,229) teach the use of a metal-on-ceramic articulation. Fisher et al teach that the difference in hardness between the metallic component and the ceramic component should be at least 4000 MPa. Khandkar et. al. specifically teach use of silicon nitride ceramic components for articulation against the metallic component. In both instances, the objective is to lower the wear of mating couples. But in both instances, the fracture risk of ceramic is still significant.

Ceramic-metal composites have also seen application in the prior art. U.S. Pat. No. 6,620,523 discloses ice skating blades made from a metal matrix composite. The ice skating blade has a titanium core and a metal composite material cladding. The metal composite material may be comprised of titanium or zirconium. U.S. Patent Application Publication No. 2004/0243241 discloses an orthopedic device, such as a spinal implant, formed of a metal matrix composite. The metal matrix composite includes a biocompatible metal alloy and a reinforcing component, such as a hard or refractory material.

However, there remains a need in the art for improved articulation joints that reduce the risk of metal ion release and the risk of monolithic ceramic fracture. There further remains a need in the art for improved articulating joints wherein one or both of the articulating surfaces are comprised of a metal matrix composite.

One particular advantage of the present invention is the reduction of the risks of fracture and metal ion release for orthopedic implants. The risks are reduced by using a graded ceramic metal composite component with ceramic surface and graded surface below the ceramic surface. As mentioned in the details of the invention, the graded ceramic metal composite of present invention provides a solution to the above described problems pertaining to currently used hard-on-hard bearings. Although the present invention is particularly applicable to hip implants, it is also useful for orthopedic implants generally. As examples of other embodiments of the invention, the composition described herein is applicable to knee and spinal implants and other implants wherein hard-on-hard articulation is desired.

BRIEF SUMMARY OF THE INVENTION

The present invention is directed to ceramic/metal composite materials for orthopedic implants generally, and more specifically, to such materials for hip implants.

In one aspect of the present invention, an orthopedic implant component comprises: a homogenous composition comprising a metallic species and a secondary phase wherein said secondary phase comprises a ceramic and wherein the average free distance between ceramic particles is less than the average size of said ceramic particles; or, a multilayered composition wherein one or more layers comprise a ceramic, a metallic species, or a combination of a ceramic and a metallic species.

In some embodiments, the ceramic is selected from the group consisting of alumina, zirconia, chromium carbide, chromium nitride, silicon carbide, silicon nitride, titanium carbide, zirconium carbide, zirconium nitride, tantalum carbide, tungsten carbide, and any combination thereof.

In some embodiments, the metallic species is selected from the alloy groups consisting of cobalt-chromium, titanium-aluminum-vanadium, zirconium-niobium and tantalum and any combination thereof.

In some embodiments, wherein said multilayered composition has a surface layer of homogeneous ceramic, and a subsurface layer comprising a metallic species and a secondary phase comprising a ceramic immediately below said surface layer and forming a boundary with said surface layer.

In some embodiments, the surface layer of homogeneous ceramic has a thickness of about 25 µm.

In some embodiments, the surface layer is 100% alumina.

In some embodiments, the surface layer is 80% alumina by volume and 20% zirconia by volume.

In some embodiments, the subsurface layer comprising a metallic species and a secondary phase comprising a ceramic is a graded layer wherein the level of ceramic decreases from an initial concentration at the boundary with said surface layer to depths further from said boundary with said surface layer.

In some embodiments, the implant component further comprises a homogenous metallic substrate layer immediately below said graded layer.

In some embodiments, the metallic substrate layer is a homogeneous cobalt-chromium alloy.

In some embodiments, the concentration at said boundary of said ceramic in said subsurface layer is 98% by volume.

In some embodiments, the implant component comprises a multilayered composition, wherein one layer comprises a combination of a ceramic and a metallic species and forms a surface of said implant component and wherein said one layer is a graded layer wherein the level of ceramic decreases from an initial concentration at said surface to depths further from said surface.

In some embodiments, the implant component comprises a multilayered composition, wherein one layer comprises a combination of a ceramic and a metallic species and forms a surface of said implant component and wherein said one layer is a graded layer wherein the level of ceramic decreases from an initial concentration at said surface to depths further from said surface, the concentration at said surface of said ceramic is 98% by volume.

In some embodiments, the implant component comprises a homogenous composition comprising a metallic species and a secondary phase wherein said secondary phase comprises a ceramic and wherein said ceramic comprises alumina.

In some embodiments, the ceramic is a mixture of alumina and zirconia.

In some embodiments, the implant component comprises a hip implant.

In some embodiments, the implant component comprises a knee implant.

In some embodiments, the implant component comprises a homogenous composition comprising a metallic species and a secondary phase wherein said secondary phase comprises a ceramic, and wherein the average free distance between ceramic particles is less than half of the average size of said ceramic particles.

In some embodiments, the implant component comprises a multilayered composition wherein one or more layers comprise a combination of a ceramic and a metallic species and wherein the average free distance between ceramic particles is less than the average size of said ceramic particles.

In some embodiments, the implant component comprises a multilayered composition wherein one or more layers comprise a combination of a ceramic and a metallic species and wherein the average free distance between ceramic particles is less than half of the average size of said ceramic particles.

In another aspect of the present invention, a method of making an orthopedic implant component having a graded composition comprises the steps of: mixing powders of ceramic components and metal components to desired ratios to form a first mixture; mixing powders of ceramic components and metal components to desired ratios to form a second mixture; laying said first mixture on said second mixture to create a first layered mixture; optionally mixing powders to form one or more additional mixtures and laying said one or more additional mixtures on said first layered mixture; and, sintering said first layered mixture or sintering a combination of said first layered mixture and said one or more additional mixtures.

In some embodiments, at least one mixing step comprises mixing using a ball milling process.

In some embodiments, at least one mixing step comprises conventional high temperature sintering.

In some embodiments, at least one mixing step comprises electric field assisted sintering.

In some embodiments, at least one mixing step comprises spark plasma sintering.

In some embodiments, the metal components have a Young's modulus in the range of about 60 GPa to about 150 GPa.

In some embodiments, the method further comprises the step of altering the size and volume fraction of ceramic particles in a ceramic/metal mixture such that the average free distance between ceramic particles is less than the size of said ceramic particles.

In some embodiments of the method, the step of altering the size and volume fraction of ceramic particles in a ceramic/metal mixture such that the average free distance between ceramic particles is less than the size of said ceramic particles comprises altering the size and volume fraction such that the average free distance between ceramic particles is less than half of the size of said ceramic particles.

Further features, aspects, and advantages of the present invention, as well as the structure and operation of various embodiments of the present invention, are described in detail below with reference to the accompanying drawings.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
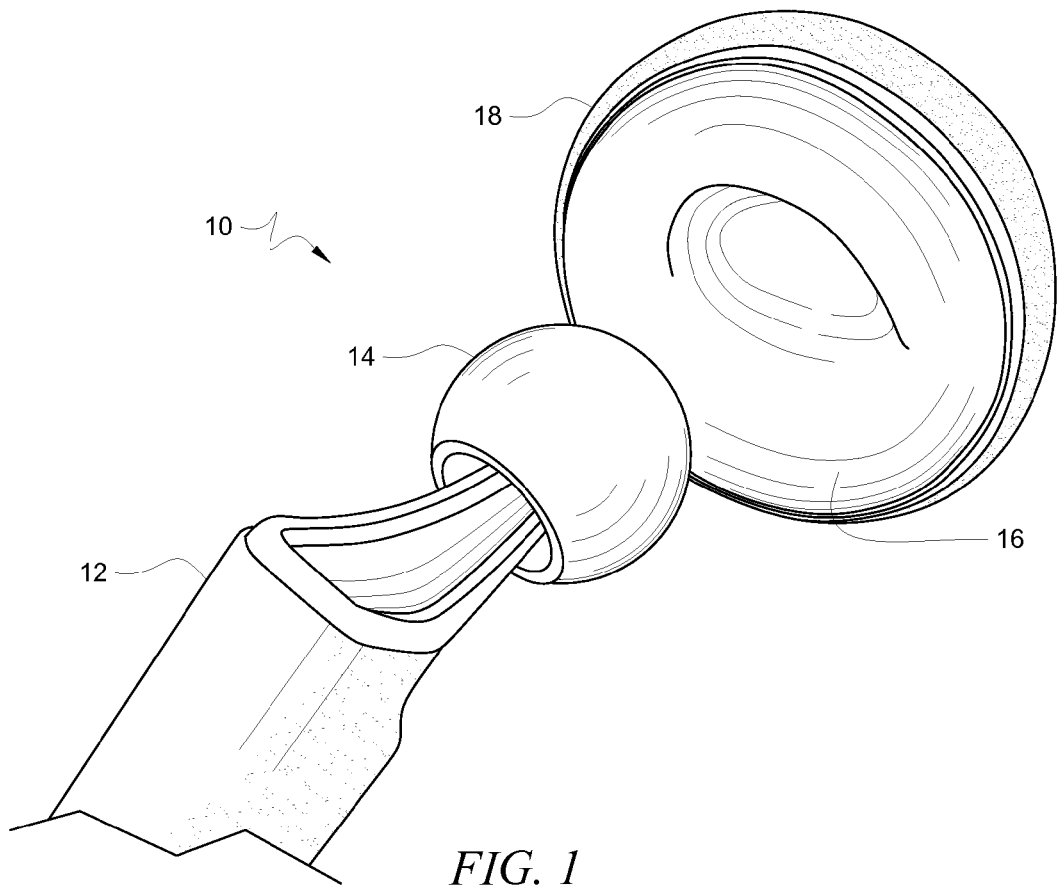
FIG. 1 illustrates a hip prosthesis which is one embodiment of the present invention.

As used herein, "a" or "an" means one or more, unless otherwise indicated. The singular encompasses the plural and the plural encompasses the singular. Thus, where reference is made to "a ceramic" or to a "ceramic component", this means one or more ceramics and one or more ceramic components, respectively. Where reference is made to "a metal" or to a "metallic species", this means one or more metals and one or more metallic species, respectively. A metallic species may be one metal or a metal alloy.

As used herein the term "homogeneous ceramic" encompasses, but is not limited to, 100% of one specific ceramic (for example, 100% alumina). In this way, the term "homogenous ceramic" also encompasses a mixture of ceramics (for example a mixture of zirconia and alumina and possibly other ceramics) so long as it is substantially free of non-ceramic components. Similarly, the term "homogeneous metal" or "homogenous metallic component" covers, but is not limited to, 100% of one specific metal (for example, 100% zirconium). In this way, the term "homogenous metal" or "homogenous metallic component" also encompasses a mixture of metals (for example a mixture of zirconium and hafnium and possibly other metals) so long as no non-metal is present.

As used herein, the term "orthopedic implant component" is defined as a portion of an entire orthopedic implant or, an entire orthopedic implant.

Wherein compositions are recited in percentages, the percentages are volume percentages, unless otherwise indicated.

The invention relates to an orthopedic implant made of a ceramic metal composite. The composite includes a first phase that is a biocompatible alloy and a second phase that is ceramic particles of carbides, nitrides, borides and/or oxides. The ceramic layer can be present on the articulating surface from about 1% to about 100% by volume (preferably from about 1% to about 100% by volume) in the metal. The volume fraction of the ceramic phase may be graded from the articulating surface of the implant to the non articulating substrate. The composite may be further hardened by allowing diffusion of nitrogen, oxygen, carbon or combination thereof. The ceramic composite may be further coated with hard coatings of carbides, nitrides, oxides, or diamond-like carbon or polycrystalline-nanocrystalline diamond coatings or amorphous diamond coatings.

The approach of the present invention is to use a ceramic metal composite where the ceramic layer is part of the metal matrix. The ceramic layer can be present from about 1% to about 100% by volume in the metal. This layer provides surface hardening to the metal, reduces metal ion release because the ceramic particles articulate against each other instead of metallic particles articulating against each other, and also mitigates the fracture risk associated with monolithic ceramics. The primary goal is to reduce metal ion release in metal-on-metal type articulation but the hardened surface can also be used for articulation against other materials.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The following description of the preferred embodiment(s) is merely exemplary in nature and is in no way intended to limit the invention, its application, or uses. Most of the following discussion focuses on hip implants for illustrative purposes, but it should be clear that the present invention is also applicable to other orthopedic implants.

FIG. 1 illustrates a hip prosthesis 10. The hip prosthesis 10 includes a stem 12, a femoral head 14, a liner 16, and a shell 18. The femoral head 14 is operatively connected to the stem 12, and the liner 16 is assembled to the shell 18. The stem 12 is adapted for mounting in a femur (not shown), and the shell 18 is adapted for mounting to an acetabulum (not shown). The femoral head 14 articulates against the liner 16.

In some embodiments of the present invention, the femoral head 14 and/or the liner 16 are made of a ceramic metal composite where the ceramic layer is part of the metal matrix. In one embodiment, a surface layer of 100% ceramic of thickness of ca. 5 to 200 μm is followed by a graded layer of ceramic/metal composite having an initial composition of 100% ceramic and decreasing to pure metal or to a steady state level of ceramic. In another embodiment, the surface composition may comprise ceramic from about 1% to nearly 100% (the surface layer having a small amount of metal). The ceramic layer can be present from about 1% to about 95% by volume in the metal. This layer provides surface hardening to the metal and the presence of ceramic particles articulating against each other reduces the metal ion release and also mitigates the fracture risk associated with monolithic ceramics. In the hip implant 10 embodiment depicted in FIG. 1, both the femoral head 14 and the liner 16 of the acetabular component 18 are made from the ceramic metal composite, but those skilled in the art would understand that in some instances only one of the components is made of the ceramic metal composite. For example, the ceramic metal composite of the femoral head 14 may articulate against a polyethylene liner, monolithic ceramic liner, or a metal liner. Alternatively, a ceramic metal composite liner 16 may articulate against a polymeric femoral head (such as one made of polyethylene), monolithic ceramic femoral head, or a metal femoral head. As those skilled in the art would understand, the term "polyethylene" includes both conventional polyethylene and cross-linked polyethylene. Also in the hip implant 10 embodiment of FIG. 1, a portion of the femoral stem 12 is illustrated for proper context. Although FIG. 1 illustrates the application of the present invention to hip implants, it should be understood that this is merely one illustrative example and that the present invention is applicable to all orthopedic implants, such as, but not limited to, knee implants, shoulder implants, elbow implants, and other implants.

The composite includes a first phase that is a biocompatible alloy (cobalt chromium based, titanium based, zirconium based, niobium based and/or tantalum based) and a second phase that is ceramic particles of carbides, nitrides, borides and oxides, such as but not restricted to chromium carbide, titanium carbide (TiC), titanium carbo-nitride (TiCN), zirconium carbide (ZrC), tantalum carbide (TaC), niobium carbide (NbC), tungsten carbide, aluminum oxide ($Al_2O_3$), and zirconium oxide ($ZrO_2$). The second phase can also include polycrystalline, amorphous and or nano-crystalline diamond grit. The composite may include one type of ceramic phase or a combination of more than two or more types of ceramic phases.

The hardness of the femoral head 14 and the liner 16 may be the same or the hardness for each component may be different. For example, the ceramic composite femoral head 14 may articulate against a monolithic ceramic liner 16 in which the hardness of the ceramic particle in the composite is different from the monolithic ceramic. As another example, the ceramic composite femoral head 14 may articulate against a ceramic composite liner 16 in which the hardness of the ceramic particle in the femoral head is different from that of the liner. The volume fraction of the ceramic phase can be varied from about 1% to about 100% in order for each of the components to have a different hardness. Alternatively, the components can be made in such a way that the volume fraction of the ceramic phase is graded from the surface of the implant to the substrate. For example, there may be approximately 100% of the ceramic phase at the surface and gradually decrease the volume fraction of the ceramic phase to less than about 1 percent at the core of the substrate. The objective of the graded composite is not to significantly affect the fracture toughness of the substrate material.

In some embodiments of the invention, this graded structure can be achieved using powder metallurgical processes. In such processes the powders of the ceramic component and the metal component are mixed and sintered. The mixing can be achieved using a ball milling process where a uniform distribution of the ceramic phase is required. Such processes are known to those of ordinary skill in the art. To obtain the graded structure, powders can be applied in the form of layers and then sintered together. The sintering of powders can be achieved using a conventional high temperature sintering process or using lower temperature electric field assisted sintering. Such sintering methods, known to those of ordinary skill in the art, as well as other sintering methods, are useful in the present invention. The temperature of the sintering will depend on the alloy composition and type of structure desired. Other alloying techniques, such as electron beam alloying of the surface, can also be done to achieve such graded structures. In one non-limiting example of the use of a powder metallurgical process, a composite structure of alumina and CoCr is made. CoCr powder is mixed with alumina powder in volume fractions ranging from 25% to 100%. These mixtures were then poured in a graphite mould as different layers. The first layer is 100% CoCr. The second layer is CoCr with 25% alumina. The third layer is 50% CoCr and 50% alumina. The fourth layer is 75% alumina and 25% CoCr. The top (surface) layer was 100% alumina. This layered structure was then sintered using a spark plasma sintering process at 1200° C. Spark plasma sintering is another sintering technique known in the art. The surface is 100% alumina and fraction of alumina decreases towards the substrate. The alumina powder had large particle size range that resulted in formation of big discontinuities in the matrix. It will be understood by those skilled in the art that the powder size and distribution can further be optimized. In such composite structure the 100% alumina is expected to be the articulating surface. Such surface is expected to eliminate the metal ion release. The graded composition ensures that the adhesion of alumina to the substrate CoCr is adequate. In the example described, the change in graded composition may be relatively abrupt. It will be understood by those skilled in the art that this change in composition can be changed from step function (more abrupt change) to linear or to any other shape desired. It will be understood by those skilled in the art, that sintering of such powder mixtures can be achieved using conventional sintering process. In one aspect of invention, such structure could also be formed by selectively melting the surface and then alloying it with ceramic particles. In another aspect, ceramic particles may be precipitated during solidification of the molten alloy. In another aspect the ceramic particles may be dispersed in a molten bath of alloy and then the mixtures is cooled to obtain uniform distribution of ceramic particles.

In some embodiments, the ceramic metal composite is formed using low modulus alloys, such as but not limited to titanium, zirconium, or niobium. The Young's modulus of these alloys typically range from about 60 to about 150 GPa. The lower modulus alloy leads to lower contact pressure and allows for the formation of thicker fluid film lubrication. The thicker fluid film reduces the wear of the articulating components. The low modulus alloy is also selected to help in getting larger clearances between the articulating components, which lowers the chances of seizure of the joint. In one aspect of invention the diametrical clearance between the mating components of the hip joint is maintained above 150 micron.

In some embodiments, the composite is engineered in such as way that the average free distance between the ceramic particles is less than the average size of the ceramic particles. This is achieved by altering the average diameter (size) of the ceramic particles and their volume fraction in the metal. The volume fraction of particles ($V_p$), the mean free distance between these particles ($\lambda$), and the average size of the particles expressed as mean intercept length ($L_3$) can be related to each other as provided below [Metals Handbook Ninth Edition, Volume 9, Metallography and Microstructures, ASM, 1989):

$$\lambda = \frac{L_3}{V_p}(1 - V_p)$$

For a known particle size ($L_3$) and desired distance between the particles ($\lambda$) a suitable volume fraction of particles ($V_p$) can be chosen as a starting point. This mixture then can be further evaluated analytically by known and standard techniques to verify the above expressed relationship. In preferred embodiments, the average free distance ($\lambda$) is less than mean intercept length ($L_3$) by at least 10%. The above process can be repeated iteratively to optimize the mean distance between the particles. The average diameter may be calculated by measuring the particle diameter of the particles through the centroid of the particles and averaging the measured diameters. For the case of non-spherical particles, the diameter may be measured through the centroid of the particles to different locations on the perimeter of the particle. For example, for an ellipsoid shaped particle, the diameter will be determined at different locations of the particle the and average of same may be determined. Standard stereological software, familiar to those of skill in the art can be used for such a purpose. In general particles can range from sub-micron sized (<1 micron) to as large as about 200 microns. Based on the particle size optical microscope or scanning electron microscope can be used to measure the particle sizes. Preferably, at least 10 to 15 fields at of view at 1000× chosen randomly are inspected. It may be required to inspect more fields of view if a magnification higher than 1000× is used. It will be understood by those skilled in the art that the accuracy and precision of such measurements can be increased by inspecting a greater number of fields. Standard guidelines known to those of ordinary skill in the art (such as, for example, the ASTM guidelines) can be used for this purpose. By controlling the average free distance between the ceramic particles, the risk of the harder ceramic articulating against the softer substrate can be reduced. In such composite, a 100% ceramic is not always necessary, although it is within the scope of the invention and may be used. In each of two or more composite components articulating against each other in an orthopedic implant, the following can be controlled independently: (1) the type of ceramic particles, (2) the volume fraction of the ceramic particles, (3) the size of the ceramic particles, (4) the size distribution of the ceramic particles, (5) the shape of the ceramic particles, and (6) the metallic substrate material. One or more types of ceramic particles with independently controlled size distributions and volume fractions can be used in the composite.

In some embodiments, the composite is engineered in such as way that the average free distance between the ceramic particles is less than the size of the ceramic particles. In some embodiments, the average free distance between the ceramic phases is less than the size of the ceramic particles. This is achieved by altering the average diameter (size) of the ceramic particles and their volume fraction in the metal. The average diameter may be calculated by averaging the multitudes of the diameter of a particle through the centroid of the particle. Standard stereological software, familiar to those of skill in the art can be used for such purpose. In general particles can range from sub-micron sized (<1 micron) to as large as about 200 microns. By controlling the average free distance between the ceramic phases, the risk of the harder ceramic articulating against the softer substrate can be reduced. In such composite the surface need not be 100% ceramic. In some embodiments, the composite is engineered in such as way that the average free distance between the ceramic particles is less than half of the size of the ceramic particles.

If the surface of such composite is not 100% ceramic then it can be further hardened by allowing diffusion of nitrogen, oxygen, carbon, or any combination thereof, using plasma or ion implantation type of processes to gain additional advantage of the hardened layer. The composite is further hardened by allowing diffusion of reactive species such as boron, carbon, nitrogen and oxygen to gain additional advantage of the hardened layer in reducing the wear of the component. The diffusion processes can be accompanied by conventional high temperature diffusion processes of reactive species or by ion implantation or by plasma assisted process. The diffusion hardened depth of such composites can range from about 1 micron to about 1000 microns.

In some embodiments, the ceramic composite is further coated with hard coatings of carbides (TiC, ZrC, TaC etc) or nitrides (TiN, ZrN, CrN etc) or oxides ($Al_2O_3$, $ZrO_2$) or borides or diamond like carbon or polycrystalline/nanocrystalline diamond coatings to reduce the metal ion release. These coatings may be applied using physical vapor or chemical vapor deposition processes. As an example, a coated femoral head may articulate against a coated or uncoated liner. Alternatively, a coated liner may articulate against a coated or uncoated femoral head.

The surface roughness of the femoral head 14 and/or the liner 16 may be specified such that the finished surface allows for maximum lubrication during articulation. Moreover, the diametrical clearance between the femoral head 14 and the liner 16 may be specified such that the finished surface allows for maximum lubrication during articulation.

Three illustrative and non-limiting embodiments of the present invention will now be described. It should be understood that these do not represent the entire scope of the invention. Modifications that will be understood by those having ordinary skill in the art are also part of the present invention. This includes the use of additional layers of material, as well as different compositional characteristics of each layer.

Figure 2:
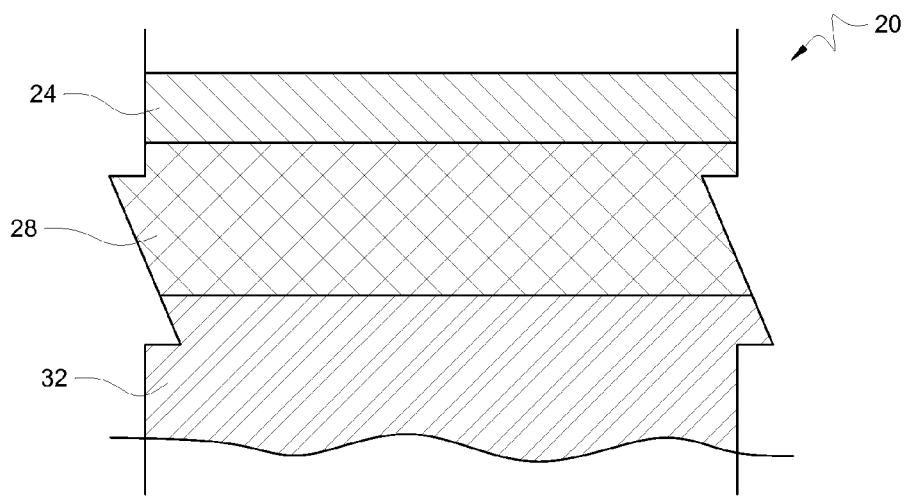
FIG. 2 shows a cross-sectional view of an example of an embodiment of a multilayered structure of the present invention.

In a first illustrative non-limiting embodiment of the present invention, in FIG. 2 there is an orthopedic implant component 20 (a cross-sectional portion of which is shown) comprising a surface layer 24 of a homogeneous ceramic material. This surface layer 24 could be, for example, 100% alumina. Alternatively, the surface layer 24 could be a mixture of ceramics, for example, 80% alumina and 20% zirconia by volume. However, other possible homogeneous ceramic materials, known to those of ordinary skill in the art also can be used. Some examples include mixtures of silicon nitride and silicon carbide, chromium carbide and titanium carbide. In general, several such combinations of ceramic particles can be made. The thickness of this ceramic surface layer 24 is preferably about 25 µm, however, other thicknesses may be used. The thickness of the ceramic layer will depend on the adhesion of the ceramic particles to each other and to the substrate at the interface. The thickness should be such that it will not de-laminate the ceramic layer from the surface. Below the homogeneous ceramic layer, there is ceramic/metal mixture comprising a graded structure 28 of metal and ceramic. In the illustrative example using alumina as a ceramic material in this second layer, the alumina would have an initial concentration which decreases monotonically as the depth from the surface increases. Preferably, the initial concentration is 95% to 99% by volume but it may be 100% by volume or some level below 95% by volume and then monotonically decreases. Below this layer, there is a homogeneous metal layer 32. In one example, the second layer 28 could have an initial concentration (directly below the first layer of homogeneous ceramic) of 95% ceramic and 5% metal by volume and decrease in ceramic content to a final concentration of 10% ceramic and 90% metal by volume. The third layer 32, which can be 100% metal by volume then begins. The thickness of the individual layers can range from 5 microns to 500 microns; the ceramic volume fraction can decrease as a step function (abrupt change) or can decrease in a linear fashion. The layers comprising ceramic/metal mixtures may be characterized by an average free distance between ceramic particles that is less than half the average size of said ceramic particles. However, this average free distance between ceramic particles is not required in multi-layered compositions.

Figure 3:
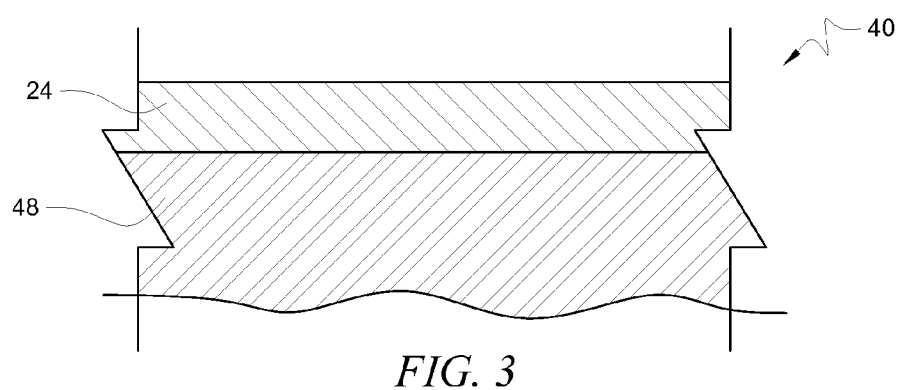
FIG. 3 shows a cross-sectional view of an example of an embodiment of a multilayered structure of the present invention.

A second illustrative non-limiting embodiment 40 is shown in FIG. 3. This embodiment differs from the first embodiment in that the second graded layer 48 decreases to some steady-state value of ceramic/metal. The second graded layer 48 is below a surface layer 24 of a homogeneous ceramic composition. In preferred embodiments, the steady-state level is primarily metallic (for example, 10% ceramic and 90% metal by volume). However, it can be primarily ceramic as well. In this embodiment, there is no discrete third layer and the final steady-state composition forms the substrate of the material. Thus, in FIG. 3 we see a structure 40 having homogeneous ceramic layer 24 and graded ceramic/metal layer 48. At some depth within layer 48, there is reached a steady-state composition of ceramic and metal which then forms the remainder of the substrate. The layers comprising ceramic/metal mixtures may be characterized by an average free distance between ceramic particles that is less than half the average size of said ceramic particles. However, this average free distance between ceramic particles is not required in multilayered compositions.

Figure 4:
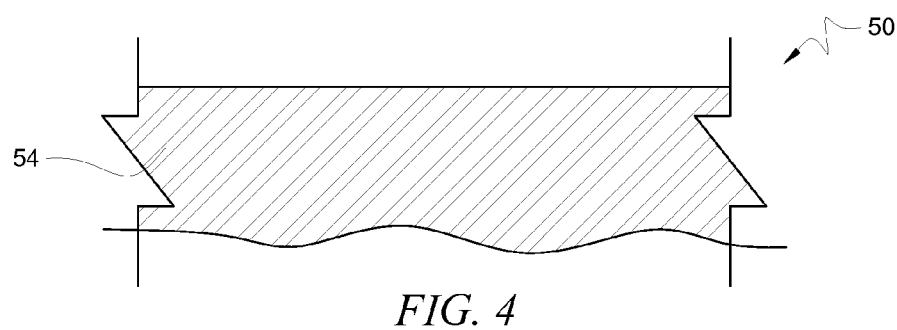
FIG. 4 shows a cross-sectional view of an example of an embodiment having a homogenous composition comprising a metallic species and a secondary phase wherein the secondary phase comprises a ceramic.

In a third illustrative non-limiting embodiment, shown in FIG. 4, the component 50 is homogeneous throughout, the sole layer 54 comprising some mixture of ceramic and metal. This mixture can be anywhere from 1% to 25% ceramic and anywhere from 99% to 75% metal. Preferably, the level is 1% to 20% ceramic and 99% to 80% metal. In this embodiment, the layers comprising ceramic/metal mixtures are characterized by an average free distance between ceramic particles that is less than half the average size of said ceramic particles.

Although the depicted embodiments illustrate the use of the ceramic metal composite in use in a hip implant, the ceramic metal composite could equally be implemented in reconstructive knee components and particularly in femoral knee components that articulate against polyethylene or other types of polymers. The invention described herein is applicable to orthopedic implants generally, and although the preferred embodiments are hip implants and knee implants, it is also applicable in, for example, shoulder, vertebral, and other orthopedic implants familiar to those of skill in the art.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An orthopaedic implant component comprising:
a unitary multilayered composition having a surface layer of a homogenous ceramic wherein an average free distance between ceramic particles is less than the average size of the ceramic particles, and a subsurface layer immediately below the surface layer, the subsurface layer comprising a ceramic and a metallic species.

2. The implant component of claim 1, wherein said ceramic within the subsurface layer is selected from the group consisting of alumina, zirconia, chromium carbide, chromium nitride, silicon carbide, silicon nitride, titanium carbide, zirconium carbide, zirconium nitride, tantalum carbide, tungsten carbide, and any combination thereof.

3. The implant component of claim 1, wherein said metallic species is selected from the alloy groups consisting of cobalt-chromium, titanium-aluminum-vanadium, zirconium-niobium and tantalum and any combination thereof.

4. The implant component of claim 1, wherein said subsurface layer forms a boundary with said surface layer.

5. The implant component of claim 4, wherein said surface layer of homogeneous ceramic has a thickness of about 25 µm.

6. The implant component of claim 4, wherein said surface layer is 100% alumina.

7. The implant component of claim 4, wherein said surface layer is 80% alumina by volume and 20% zirconia by volume.

8. The implant component of claim 4, wherein said subsurface layer is a graded layer wherein the level of ceramic decreases from an initial concentration at the boundary with said surface layer to depths further from said boundary with said surface layer.

9. The implant component of claim 8, further comprising a homogenous metallic substrate layer immediately below said graded layer.

10. The implant component of claim 9, wherein said metallic substrate layer is a homogeneous cobalt-chromium alloy.

11. The implant component of claim 4, wherein a concentration at said boundary of said ceramic in said subsurface layer is 98% by volume.

12. The implant component of claim 1, wherein said subsurface layer is a graded layer wherein the level of ceramic decreases from an initial concentration at said surface layer to depths further from said surface layer.

13. The implant component of claim 12, wherein a concentration at said surface of said ceramic is 98% by volume.

14. The implant component of claim 1, wherein said ceramic of the subsurface layer comprises alumina.

15. The implant component of dam 14, wherein said ceramic is a mixture of alumina and zirconia.

16. The implant component of claim 1, wherein said implant component comprises a hip implant.

17. The implant component of claim 1, wherein said implant component comprises a knee implant.

18. The implant component of claim 1, wherein the average free distance between ceramic particles of the subsurface layer is less than half of the average size of said ceramic particles.

19. The implant component of claim 1, wherein the average free distance between ceramic particles of the subsurface layer is less than the average size of said ceramic particles.

20. The implant component of claim 1, wherein the average free distance between ceramic particles of the homogeneous layer is less than half of the average size of said ceramic particles.

* * * * *